(12) United States Patent
Levecq

(10) Patent No.: US 9,232,891 B2
(45) Date of Patent: Jan. 12, 2016

(54) METHOD AND DEVICE FOR HIGH-RESOLUTION RETINAL IMAGING

(75) Inventor: Xavier Levecq, Gif sur Yvette (FR)

(73) Assignee: Imagine Eyes, Orsay (FR)

(*) Notice: Subject to any disclaimer, the term of this patent is extended or adjusted under 35 U.S.C. 154(b) by 113 days.

(21) Appl. No.: 14/000,613

(22) PCT Filed: Feb. 21, 2012

(86) PCT No.: PCT/EP2012/052933
§ 371 (c)(1),
(2), (4) Date: Oct. 29, 2013

(87) PCT Pub. No.: WO2012/113790
PCT Pub. Date: Aug. 30, 2012

(65) Prior Publication Data
US 2014/0049749 A1 Feb. 20, 2014

(30) Foreign Application Priority Data
Feb. 22, 2011 (FR) .................................... 11 51440

(51) Int. Cl.
*A61B 3/10* (2006.01)
*A61B 3/15* (2006.01)
*A61B 3/14* (2006.01)

(52) U.S. Cl.
CPC ............... *A61B 3/158* (2013.01); *A61B 3/1015* (2013.01); *A61B 3/14* (2013.01)

(58) Field of Classification Search
CPC .......... A61B 3/0008; A61B 3/00; A61B 3/15; A61B 3/112; A61B 3/1173
USPC .......................... 351/207, 221, 246, 206, 205
See application file for complete search history.

(56) References Cited

U.S. PATENT DOCUMENTS

| 5,430,507 | A | * | 7/1995 | Nishio et al. .................. 351/208 |
| 2003/0058403 | A1 | | 3/2003 | Lai et al. |
| 2007/0258045 | A1 | | 11/2007 | Yamaguchi et al. |

FOREIGN PATENT DOCUMENTS

| EP | 1561416 A1 | 8/2005 |
| WO | 01/58339 A2 | 8/2001 |

(Continued)

OTHER PUBLICATIONS

Hofer et al.; "Improvement in Retinal Image Quality with Dynamic Correction of the Eye's Aberrations;" Optics Express, vol. 8, No. 11; May 21, 2001 (13 pages).

(Continued)

*Primary Examiner* — Hung Dang
(74) *Attorney, Agent, or Firm* — Osha Liang LLP

(57) ABSTRACT

The invention relates, according to one aspect, to a retinal imaging device including at least one source ($LS_a$, $LS_r$) for emitting a light beam in order to illuminate the retina of an eye (10) of a subject, a retinal imaging path including a detection device (12) having a detection plane (121) and an optical imaging system (L1, L5, L6), an analysis path including a device (15) for measuring optical defects having an analysis plane (151) for receiving a set of light rays backscattered by the retina and optical means for adjoining said analysis plane and a predetermined plane in the input space of said imaging system of the imaging path, a correction device (14) shared by said analysis and imaging paths, which includes a correction plane (141) and which is intended to correct, in said correction plane, the light rays from said emission source and backscattered by the retina according to the optical defects measured by the device for measuring optical defects. The retinal imaging device further includes a light blackout system (20), which is positioned in an adjacent plane or which coincides with said correction plane, or which is positioned in an image plane of said correction plane located on an optical path shared by the analysis and imaging paths, and which is sized so as to at least partially black out the reflections of the light rays from said emission source by the corneal surface.

16 Claims, 5 Drawing Sheets

(56) References Cited

FOREIGN PATENT DOCUMENTS

| WO | 2007/035334 A2 | 3/2007 |
| WO | 2010/083381 A1 | 7/2010 |

OTHER PUBLICATIONS

Roorda et al.; "Adaptive Optics Scanning Laser Opthalmoscopy;" Optics Express, vol. 10, No. 9; May 6, 2002 (8 pages).
Zawadzki, Robert J.; "Adaptive-optics Optical Coherence Tomography for High-resolution and High-speed 3D Retinal In Vivo Imaging;" Optics Express, vol. 13, No. 21; Oct. 17, 2005 (15 pages).
Roorda, Austin; "Adaptive optics Opthalmoscopy;" Journal of Refractive Surgery, vol. 16; Sep./ Oct. 2000 (6 pages).
International Search Report issued in PCT/EP2012/052933 mailed on May 15, 2012 (6 pages).
Written Opinion of the International Searching Authority issued in PCT/EP2012/052933 mailed on May 15, 2012 (8 pages).

* cited by examiner

METHOD AND DEVICE FOR HIGH-RESOLUTION RETINAL IMAGING

TECHNICAL FIELD OF THE INVENTION

The present invention relates to a retinal imaging method/device having a resolution compatible with cellular-scale imaging, and based on the use of adaptive optics.

PRIOR ART

At the present time several years pass between the onset of a retinal disease and its diagnosis. This is because in general the first clinical symptoms of retinal diseases do not manifest before the unnoticed development of the disease has caused irreversible lesions to form. This is the case, for example, of age-related macular degeneration (AMD); or glaucoma, a disease that attacks the nerve fibers of the retina and that can cause blindness in the subject, and which is generally diagnosed when half the nerve fibers of the subject have already been irreparably destroyed. However, retinal diseases can be diagnosed in the first weeks after onset if it is possible to image the retina at the cellular scale. This is because retinal diseases initially affect microscopic retinal structures. The microstructures affected by the 3 commonest retinal maladies (AMD, glaucoma, diabetic retinopathy), which are among the most severe, are photoreceptor cells, including cone photoreceptors, photosensitive cells that detect light and that are between 2 and 5 µm in size; the microvessels of the retina, which are the smallest vessels of the human body (about 6 µm in diameter); and bundles of nerve fibers that have a diameter of about 10 µm.

Many laboratories are working on various technologies that would allow retinal imaging to carried out with cellular resolution. These various technologies employ different systems for illuminating and/or detecting the retina but all use adaptive optical systems, allowing the optical defects of the eye and of the imaging system to be measured and the light rays coming from the retina and incident on the detecting system to be corrected in order to increase resolution.

Among these technologies, mention may be made of adaptive optics scanning laser ophthalmoscopy (AOSLO).

An AOSLO assembly is for example described by A. Roorda et al. in "Adaptive optics scanning laser ophthalmoscopy", Optics Express 405, Vol. 10, No. 9, 2002. The AOSLO assembly mainly comprises a system for illuminating the retina; a detecting device; a scanning system; a correcting system comprising a plane for correcting incident light waves; a system for measuring optical defects, comprising a plane for analyzing optical defects in incident light rays; and imaging optics. The illuminating system for example comprises a laser diode coupled to an optical fiber, in order to form a point source, and an optical lens allowing an illuminating beam to be formed from the point source. The illuminating beam is transmitted, for example by a set of mirrors, to the correcting system, for example a deformable mirror, then to the scanning system in order to be scanned vertically and horizontally over the eye of the subject. The illuminating beam is thus focused in order to form a quasi-spot beam that is scanned over the retina, and the light backscattered by the retina undergoes the same optical scanning on return in order to be transmitted to the deformable mirror and detecting device, for example comprising a confocal sensor hole and a detector that may be a photomultiplier or an avalanche photodiode. A set of optical elements allows the plane of the retina and the detecting plane, which is the plane of the confocal sensor hole of the detector, to be optically conjugated. The system for measuring optical defects for example comprises a Shack-Hartmann analyzer; it receives light backscattered by the retina and controls the deformable mirror in order to correct the illuminating beam and the backscattered beam. The illuminating system may comprise a first source that emits a beam for imaging, and a second source that emits a beam for analyzing optical defects, the latter source being separate from the imaging source, or these two sources may be combined, the same retina-illuminating beam being used for imaging and analysis.

Optical coherence tomography (OCT) assemblies that are coupled to adaptive optics are also known. Such a system is for example described by R. Zawadzki in "Adaptive-optics optical coherence tomography for high resolution and high speed 3D retinal in vivo imaging" Optics Express 8532, Vol. 13, No. 21, 2005. OCT is based on the use of a low coherence interferometer. This imaging technique allows cross-sectional images of tissue to be produced in vivo with a resolution of a few microns. OCT assemblies comprise an arrangement similar to that of AOSLOs, but in which the detecting system is specific to OCTs and especially comprises an interferometer, for example a fiber interferometer, for example a Michelson interferometer. The detecting plane is the plane comprising the point of entrance to the fiber; this plane is conjugated with the retina of the eye by means of an optically conjugating system. One benefit of OCT in ophthalmology stems from its capacity to image in vivo tissue through other scattering tissues. In comparison with AOSLO, OCT technology makes it possible to obtain a longitudinal cross section through the retina to the detriment of acquisition speed.

A third known technique is full-field or 'flood' retinal imaging, for example described by H. Hofer et al. in "Improvements in retinal image quality with dynamic correction of the eye's aberrations", Optics Express, Vol. 8, Issue 11, pp. 631-643, 2001; or by A. Roorda in "Adaptive Optics Ophthalmoscopy", Journal of Refractive Surgery, Vol. 16, 2000. Relative to OCT or AOSLO systems, the depth to which the retina can be explored with flood type retinal imaging devices is limited, but they have the advantage of operating in full-field mode, i.e. there is no mechanical scanning of the retina, and with much shorter total image acquisition times, thereby making them less complex to produce, less expensive and less sensitive to deformation of the image during the acquisition time, which deformation is generated by movement of the retina.

A prior-art full-field retinal imaging assembly is illustrated in FIG. 1. It comprises, as is generally the case, an illuminating unit 11 with a first illuminating source $LS_r$ for imaging the retina, and a second illuminating source $LS_a$ for analysis of optical defects. It also comprises a detecting unit 12 comprising a multi-detector (or matrix detector) acquisition device, for example a CCD camera, the detecting plane 121 of which is intended to be optically conjugated with the retina of the eye 10 to be imaged by virtue of the image-forming optical system (or imaging system) containing, in this example, a set of objective lenses $L_1$, $L_5$, $L_6$ and beam splitters. The imaging system forms, with the detector, the imaging channel. The required field of the retina is intended to be illuminated by beams originating from the imaging source $LS_r$ and transmitted to the retina by means of a set of objective lenses $L_4$, $L_3$, $L_2$ and the beam splitter $BS_1$. A correcting device 14, for example a deformable mirror, comprising a plane 141 for correcting light rays backscattered by the retina, controlled by a system 15 for measuring optical defects, allows all or some of the optical defects due to the eye and to the optical system of the imaging system to be corrected and thus the quality of the image of the retina formed in the detecting unit 12 to be improved. The system for measuring optical defects allows optical defects in an incident light wave to be determined in an analysis plane in one measurement. In the rest of the description, the expression "optical defects" will be understood to mean all of the interference that light rays undergo between the retina and the analysis plane. These defects especially comprise defects introduced by the optical system of the eye, but also those introduced by the part of the imaging system shared with the analysis channel. The system 15 for measuring optical defects is advantageously a Shack-Hartmann analyzer comprising an analysis plane 151 formed from an array of microlenses and a matrix detector arranged in the focal plane of said microlenses. It receives a wave originating from the illuminating point source $LS_a$, which wave is focused on the retina by means of a set of objective lenses $L_2$, $L_4$ and beam splitters $BS_2$, $BS_1$, in order to form a secondary point source, then backscattered towards the analyzing system. In the system, the analysis plane of the optical-defect analyzer and the correcting plane of the correcting device are optically conjugated with a preset plane in the entrance space of the imaging system i.e. a real plane intended to be coincident with a preset plane of the eye, for example the pupillary plane of the eye. The entrance pupil of the imaging system is advantageously located in the same preset plane in the entrance space of the imaging system. The analysis channel is thus formed from the system 15 for measuring optical defects, and the means for conjugating the analysis plane with said preset plane in the entrance space of the imaging system. The entrance pupil of the imaging system is for example an image of the physical pupil of the correcting device, which pupil is formed, for example, by a diaphragm and defining the useful area of the correcting device. Generally, for an optical system, the expression "entrance pupil" is understood to mean the smallest aperture that limits the entrance or propagation of light rays into the system. This aperture may be real in the case where a physical diaphragm, pupil of the optical system considered, limits the entrance of light rays, or virtual in the case where this aperture is an image of the physical pupil of the optical system, located inside the optical system and, for example, formed by a diaphragm. Thus, in the case where the entrance pupil of the imaging system of the retina is positioned in the pupillary plane of the eye, or in a plane located near the latter, said entrance pupil is virtual, it is an image of a physical diaphragm located inside said imaging optical system. As is illustrated in FIG. 1, it is sought, in a high-resolution system, to maximize the optical path common to the analysis channel and the imaging channel in order to minimize differential optical defects between these two channels and in order to prevent optical defects located in the analysis channel (not present in the imaging channel) from being taken into account in the correction, and in order not to overlook optical defects located in the imaging channel (not present in the analysis channel).

However, a full-field retinal imaging device such as described in FIG. 1 sees its resolution limited by parasitic reflections from the cornea. Specifically, corneal reflection, i.e. reflection by the cornea of the beams originating from the imaging light source, adds a continuous background to the useful light signal at the pupillary plane, thereby introducing noise into the detecting system, which noise contributes to a decrease in signal-to-noise ratio and therefore to degradation of image quality. On account of the fact that this corneal reflection occurs in a plane near the pupillary plane and therefore far from the imaging plane, this reflection leads to a light flux that is relatively uniformly distributed over the detector. This parasitic flux generates additional photonic noise that decreases the signal-to-noise ratio of the image obtained. By way of example, the reflection coefficient of the cornea is given by the formula $(n_c-1)^2/(n_c+1)^2$ where $n_c$ is the refractive index of the tear film on the cornea, i.e. about 1.3. The reflection coefficient is therefore 1.7%. However, the ratio of the recovered flux containing the useful signal to the flux transmitted to the eye by the imaging source is between $\frac{1}{50000}$ and $\frac{1}{100000}$. In order to optimize the quality of the image it is therefore necessary to minimize this corneal-reflection-related parasitic flux.

The problem of how to block corneal reflections is a problem that those skilled in the art have already tried to solve. In particular, it has been suggested to form an image using an annular beam to illuminate the periphery of the ocular pupil (see, for example, U.S. Pat. No. 3,594,071 in the field of cameras for imaging the back of the eye). In this configuration, the entrance pupil of the imaging system is centered on the middle of the ocular pupil and corneal reflection does not interfere with the imaging. It is also possible to envision off-axis illumination for the analysis channel in order to prevent the apex of the retina from being illuminated, thereby, with coupling to a filtering hole in the retinal plane, allowing corneal reflections to be blocked.

However, neither of these approaches can be adopted for high-resolution imaging of the photoreceptor layer of the retina. This is because, in order to image cones (photoreceptors) with a good contrast it is necessary to optimize the imaging system in order to take account of the Stiles-Crawford effect, as is described, for example by A. Roorda in "Adaptive Optics Ophthalmoscopy", Journal of Refractive Surgery, Vol. 16, 2000. This effect, which is related to the geometry of the cone photoreceptors, means that the reflectivity of these photoreceptors depends on the angle of incidence of the light rays illuminating the retina. Thus, it would be better, in order to optimize the imaging system, for the angle of attack of the rays on the photoreceptors to be as small as possible. Annular illumination, such as used in the prior art, implies a high angle of incidence of the rays on the photoreceptors, preventing use being made of the Stiles-Crawford effect. In contrast, an optimized Stiles-Crawford effect requires the illumination to be substantially centered on the apex of the cornea in order to minimize the angle of incidence of the light rays on the layer of photoreceptors. Thus, high-resolution imaging of the retina requires the illumination to be centered on the optical axis of the eye. Moreover, off-axis illumination for the analysis channel, apart from the fact that it also does not optimize the Stiles-Crawford effect, requires spatial filtering to be carried out in a plane conjugated with the plane of the retina, in order to block corneal reflections, thereby running the risk that the imaged field of the retina will be limited if this filtering is carried out in a common part of the imaging and analysis channels, it being desired to maximize this common part.

Document US 2007/0258045 describes an ophthalmological imaging apparatus in which a drilled mirror is arranged, in a high-resolution imaging channel, in order to cut out some of the parasitic reflections originating from the apex of the cornea. However, the system such as disclosed in this document necessarily introduces errors into the measurement of the optical defects carried out by the wavefront analyzer, due to parasitic reflections in the analysis channel, errors that will mar the quality of the image.

One object of the invention is to provide a retinal imaging device that removes or greatly decreases the influence of corneal reflections, both in the imaging plane and in a plane near an image of the pupillary plane of the eye, without causing a malfunction or a loss of performance. In particular, one object of the present invention is to take into account the new dimension of adaptive optics (i.e. correction of optical defects) in a high-resolution retinal camera.

SUMMARY OF THE INVENTION

According to a first aspect, the invention relates to a retinal imaging device comprising:
- at least one source for emitting a light beam for illuminating the retina of an eye of a subject;
- an imaging channel for imaging the retina, comprising a detecting device with a detecting plane, and an imaging optical system;
- an analysis channel, comprising a device for measuring optical defects, with an analysis plane intended to receive a set of light rays backscattered by the retina, and means for optically conjugating said analysis plane with a preset plane in the entrance space of the imaging system of the imaging channel;
- a correcting device common to said analysis and imaging channels, comprising a correcting plane, and intended to correct, in said correcting plane, the light rays originating from said emitting source and backscattered by the retina, depending on the optical defects measured by the measuring device; and
- a system for blocking light, positioned in a plane neighboring or coincident with said correcting plane, or in an image plane of said correcting plane located on an optical path common to the analysis and imaging channels, and dimensioned to at least partially block reflection by the cornea of light rays originating from said emitting source.

The Applicant has demonstrated that by arranging a blocking system in the correcting plane, or in a plane conjugated with the correcting plane if this conjugated plane is on an optical path common to the analysis and imaging channels, it is possible to considerably decrease the influence of the reflections both on the imaging and on the analysis, without degrading the performance of the system; on the contrary, the performance of the system is improved because of the better signal-to-noise ratio obtained for both channels.

Advantageously, the correcting plane is itself conjugated with the preset plane in the entrance space of the imaging system of the imaging channel, said preset plane for example being the plane of the entrance pupil of the imaging system.

Advantageously, the blocking system takes the form of an opaque disk the diameter of which, projected into the entrance space of the imaging system, is greater than or equal to a value d given by $d = \tan \theta \times R/2$, where R is the radius of curvature of the cornea and $\theta$ is the angular diameter of the emitting source.

Advantageously, the blocking system is centered on the optical axis of said imaging optical system. This configuration is the most advantageous, especially when the center of the cornea is centered on the pupil of the eye, which it will be sought to center on the entrance pupil of the imaging optical system.

In one embodiment, the correcting device comprises a deformable mirror. Alternatively, a liquid-crystal valve may be used.

In one embodiment, the device for measuring optical defects is a Shack-Hartmann analyzer.

Advantageously, the retinal imaging device furthermore comprises a system for positioning the imaging device in space relative to the eye, making it possible to ensure the blocking system is centered on the image formed by the corneal surface of the imaging source.

For example, the retinal imaging device is of the full-field type, comprising an imaging first light source for illuminating a given field of the retina, and an analysis second light source for illuminating the retina for the purpose of analyzing optical defects with said device for measuring optical defects, the detecting device comprising a matrix detector and the blocking system being dimensioned to at least partially block reflection by the corneal surface of the light rays originating from said sources.

According to a second aspect, the invention relates to a retinal imaging method, comprising:
- emitting at least one light beam in order to illuminate the retina of an eye of a subject, by means of a light-emitting source;
- forming an image of at least one part of the retina on a detecting plane of a detecting device, by means of an imaging optical system defining an imaging channel;
- measuring optical defects by analyzing, in a given analysis plane, optical defects in light rays backscattered by the retina, said analysis plane being conjugated with a preset plane of the eye by means of an optically conjugating system defining an analysis channel;
- correcting, in a given correcting plane, light rays originating from said emitting source and backscattered by the retina, depending on the measured optical defects; and
- at least partially blocking reflection by the corneal surface of light rays originating from said emitting source using a system for blocking light flux, said system being arranged in a plane neighboring the correcting plane, or in a plane conjugated with the correcting plane located on a path common to the analysis and imaging channels.

Advantageously, the correcting plane is conjugated with said preset plane of the eye and said preset plane of the eye is substantially coincident with the image plane of said imaging source formed by the corneal surface, thereby allowing the size of the blocking zone required to block rays reflected by the corneal surface, which rays originate from the imaging source, to be minimized.

Advantageously, said preset plane of the eye is the plane of the entrance pupil of the imaging system.

Advantageously, the beams originating from said source(s) for illuminating the retina are incident into the eye via the apex of the cornea of the eye, thus allowing the Stiles-Crawford effect to be optimized.

Advantageously, the retinal imaging method furthermore comprises positioning the imaging system in space relative to the eye.

As a variant, the retinal imaging method is a full-field method and comprises emitting an imaging first light beam in order to illuminate a given field of the retina, and emitting a second light beam for illuminating the retina in order to analyze optical defects, and at least partially blocking reflection by the corneal surface of said imaging and analysis light beams using said blocking system.

BRIEF DESCRIPTION OF THE DRAWINGS

Other advantages and features of the invention will become apparent on reading the description, which is illustrated by the following figures.

For the sake of consistency, identical elements have been referenced with the same references in the various figures.

DETAILED DESCRIPTION

Figure 1:
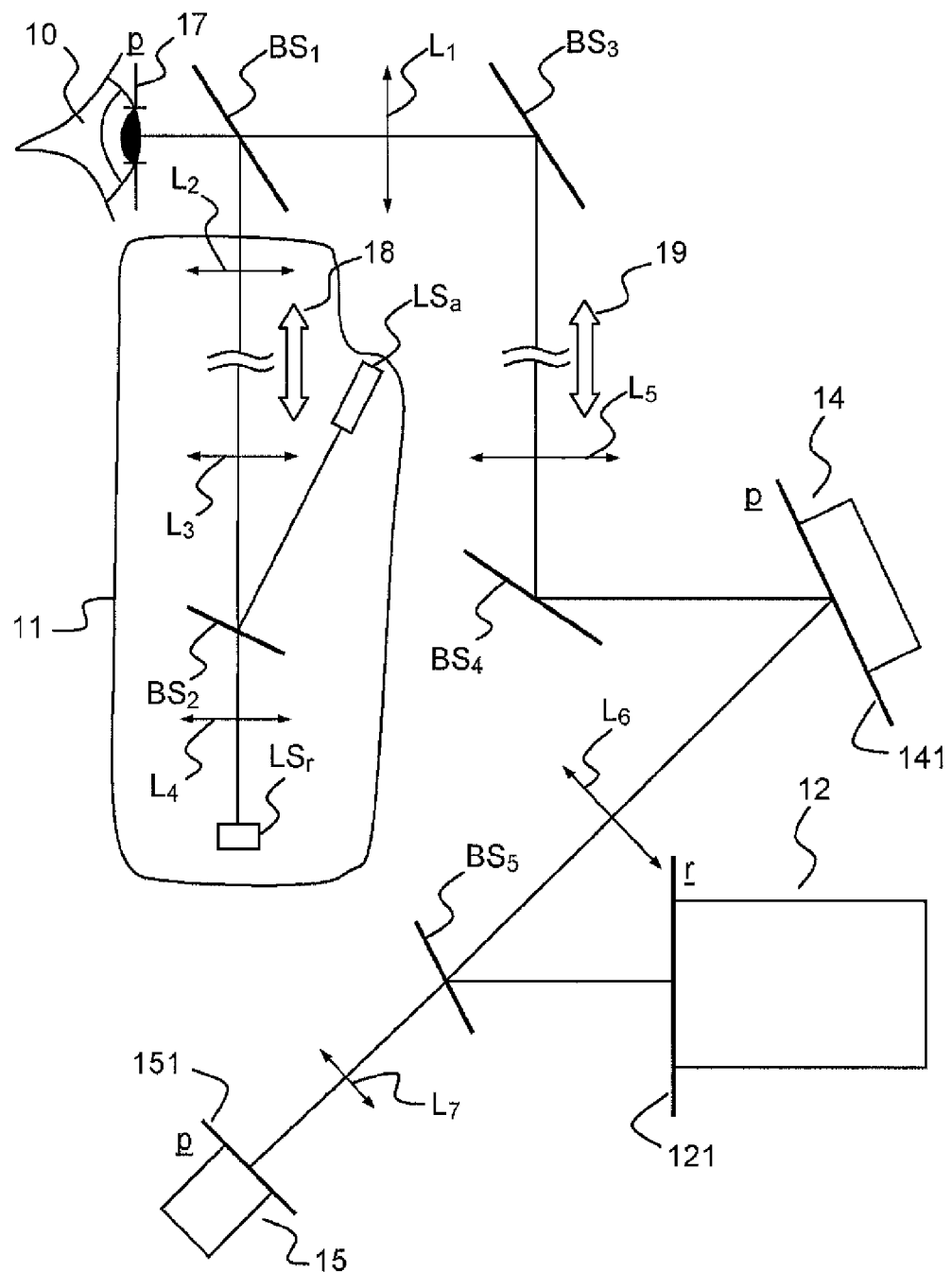
FIG. 1 (described above), a prior-art full-field retinal imaging system.
Figure 2:
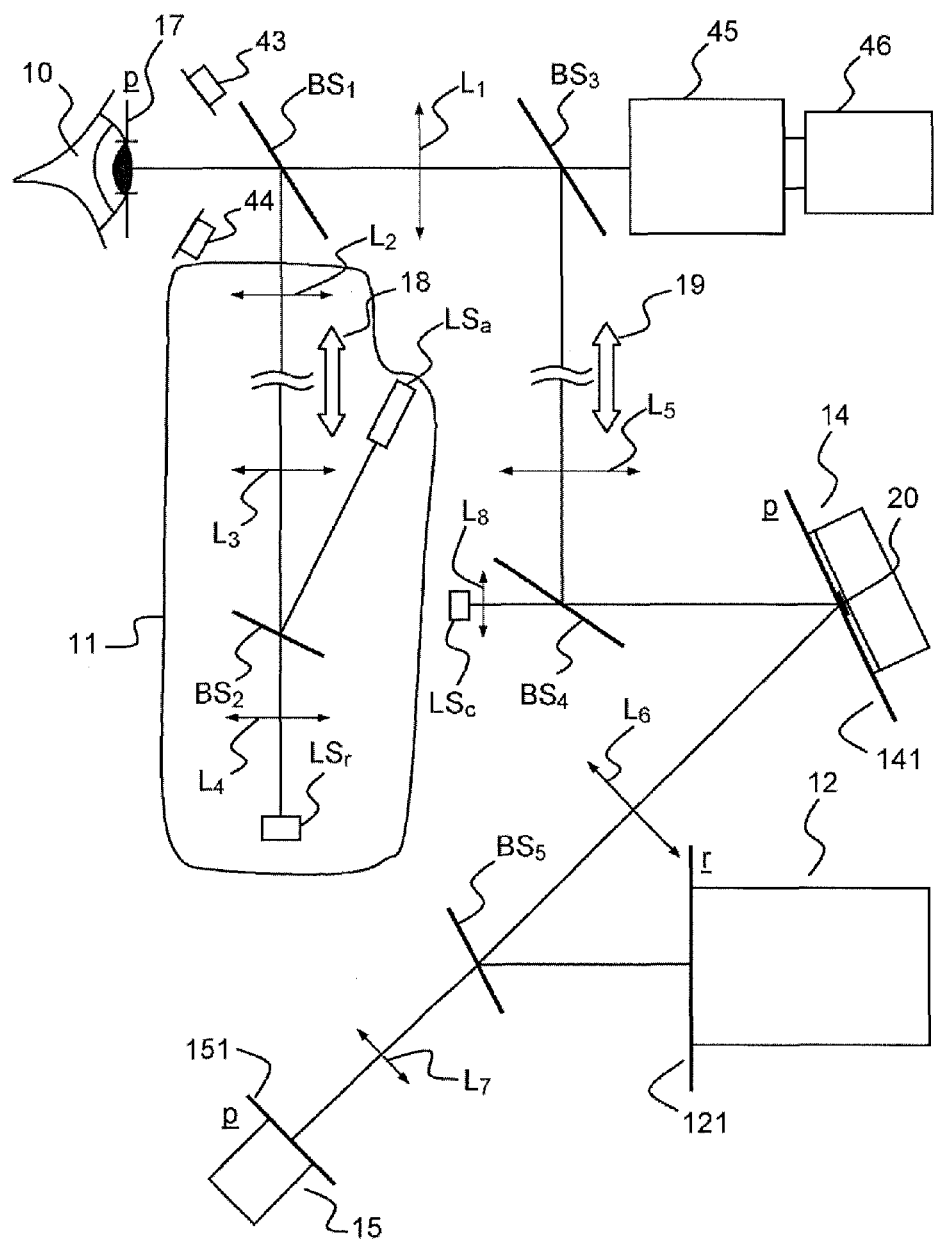
FIG. 2, an embodiment of a full-field imaging system according to the invention.

FIG. 2 shows an example high-resolution retinal imaging device according to one embodiment of the invention. In FIG. 2, only those elements of the device required to understand the invention have been shown. The imaging device comprises an illuminating unit 11, comprising a first source $LS_r$, for emitting a light beam intended to illuminate the retina of an eye 10 of a subject in order to form an image thereof by means of the detecting unit 12. This source allows a given field θ of the retina of the eye to be illuminated, typically 4°×4° for a "full-field" image. Advantageously, the source $LS_r$ for illuminating the retina emits in a spectral band in the near infrared, typically between 750 and 1100 nm, this wavelength range providing the subject with greater ocular comfort and penetrating further into the layers of the retina. As one variant, the source $LS_r$ for illuminating the retina may also emit in the visible in order to produce color images of the retina. Wavelengths in the blue or the near ultraviolet, typically between 350 and 500 nm, may also be used to visualize bundles of nerve fibers, for example in the context of glaucoma diagnosis. The source $LS_r$ is for example an LED or a lamp equipped with a filter. The illuminating unit 11 also comprises a second source $LS_a$ for illuminating the retina, which source is intended to be used to analyze optical defects in the imaging system. The illuminating source $LS_a$ is a point source, allowing a secondary point source to be formed on the retina of the eye of the subject. Typically, the wavelength of the source $LS_a$ providing illumination for optical defect analysis is about 750 nm. Such a wavelength is comfortable for the subject and also as near as possible to the imaging wavelength. Preferably, the wavelength of the source $LS_a$ is different from that of the source $LS_r$ in order to separate of the optical paths of the optical-defect measurement and the retinal imaging. The source $LS_a$ is for example a laser diode or a superluminescent diode SLD. A set of beam splitters $BS_1$, $BS_2$, allows the light beams emitted by the sources $LS_r$ and $LS_a$ to be transmitted to the eye 10 of the subject. A set of optical elements $L_2$, $L_3$, $L_4$, are used to form collinear beams from the illuminating sources, which beams are incident on the pupil of the eye. The image of the retina is formed on a detecting plane 121 of the detecting unit 12, for example comprising an imaging camera such as a charge coupled device (CCD), by means of an imaging system especially comprising, in this example, a set of optical elements referenced $L_1$, $L_5$, $L_6$, the deformable mirror and a set of beam splitters. The detecting plane is, in this example, the plane of the sensing elements of the imaging camera. Badal type systems 18 and 19 make it possible to compensate for subject ametropia while ensuring pupillary conjugation between the preset plane of the eye 17 and the analysis and correcting planes. The imaging system has an entrance pupil located in a real plane in the entrance space of the imaging system, which plane is intended to be coincident, during examination of an eye of a subject, with a preset plane 17 of the eye, for example the pupillary plane. The entrance pupil is sufficiently large to allow a sufficiently high theoretical resolution, especially with respect to the visualization of cones, to be obtained. Typically, it is about 5 to 7 mm. In FIG. 2, the planes referenced by the letter "r" correspond to planes optically conjugated with the plane of the retina, whereas planes referenced by the letter "p" correspond to planes optically conjugated with said preset plane 17. The retinal imaging device furthermore comprises a device 15 for analyzing optical defects. It is a question of analyzing, as best as possible, all the interference that the light rays encounter between the retina and the detector. The device for analyzing optical defects is, for example, a Shack-Hartmann analyzer (HASO® 32-eye Imagine Eyes®) comprising an analysis plane formed from an array of microlenses, and a detector placed in the focal plane of the microlenses. The analysis plane is advantageously optically conjugated with the plane 17 of the entrance pupil of the imaging system by virtue of optically conjugating means, especially comprising the optical elements $L_1$, $L_5$, $L_6$, $L_7$; the deformable mirror; and a set of beam splitters. It is thus possible to define an imaging channel, especially comprising the detector 12 and the imaging system intended to form the image of the retina on the detecting plane of the detector. It is also possible to define an analysis channel, especially comprising the device 15 for measuring optical defects, and the means for optically conjugating the analysis plane with the plane 17 of the entrance pupil of the imaging system. The deformable mirror is located on an optical path common to both channels. A computer (not shown) allows the optical defects in the system to be determined and transmits a correction control signal to the correcting device 14, for example a deformable mirror such as the mirao 52-e Imagine Eyes® may be used. Advantageously, the plane of the deformable mirror is also optically conjugated with the plane 17 of the entrance pupil of the imaging system. A set of beam splitters, referenced $BS_3$, $BS_4$, $BS_5$ in FIG. 2, enables the light rays originating from the illuminating sources $LS_r$ and $LS_a$ and backscattered by the retina to be directed onto the deformable mirror 12 and then onto the detector 12 and analyzer 15, respectively, these rays forming imaging and analysis beams, respectively. As a variant, the entrance pupil 17 of the imaging device is an image of the pupil in the deformable mirror.

In the example illustrated in FIG. 2, a blocking system, formed here by a blocking dot 20, is positioned in or near the correcting plane of the correcting device 14 and centered on the optical axis of the imaging system. The optical axis is generally defined as the axis joining the center of the entrance pupil of the imaging system to the center of the field. The dot is dimensioned in order to allow reflection of the beams, originating from the imaging and analysis sources, from the cornea to be blocked.

The correcting plane (or an image of the latter) is a plane with particular characteristics. Specifically, it is in this plane that partial blocking of the pupil affects the beam for analyzing optical defects and the imaging beam in the same way. More precisely, the part of the correcting device (for example a deformable mirror) not seen by the system for measuring optical defects, because the analysis beam is blocked by the blocking system, cannot be controlled. In other words, the correction applied by the correcting element in this part is not controlled. It is therefore important for this uncontrolled part of the correcting element not to interact with that beam, illuminating the retina, which serves to create the image of the retina, whatever the angular diameter of the illuminated zone. A "blocking" plane that ensures the above constraint is met is the correcting plane of the correcting element itself (or a plane in its immediate vicinity) or a plane conjugated with the latter, insofar as this conjugated plane is located on a part common to the imaging system and the system for measuring optical defects.

Advantageously, the correcting plane will be arranged in order to be substantially conjugated with the image plane of the illuminating source formed by the corneal surface, during imaging of the retina of a subject. It turns out that this plane is located very near the pupillary plane of the eye, thereby allowing, in fine, a system for measuring and correcting optical defects to be obtained, the analysis and correcting planes of which are substantially optically conjugated with the pupillary plane of the eye, which proves to be an advantageous configuration for obtaining a good correction of optical defects, not only on-axis but also in the imaging field, without generating an aperture effect in the flux backscattered by the retina.

Alternatively, the correcting plane will possibly be arranged in such a way that it is substantially conjugated with the image plane of the analysis source formed by the corneal surface, if the image planes formed by the corneal surface of the imaging and analysis sources are not coincident, or located in an intermediate position between the two image planes, depending on which of the sources it is desired to minimize reflections for.

The "blocking" diameter of the blocking system, in the example in FIG. 2 the diameter of the spot 20, may be calculated to be at least as large as the size of the image formed by the cornea of the source illuminating the retina, multiplied by the magnification factor between the plane of the image of the source formed by the cornea and the plane of the blocking system. Since the analysis source is a quasi-point source, the size of its image formed by the corneal surface is smaller than that of the source illuminating the retina, and with a blocking system dimensioned to block reflection from the cornea of the beams originating from the imaging source, reflection of the beams originating from the analysis source are also blocked.

Figure 3:
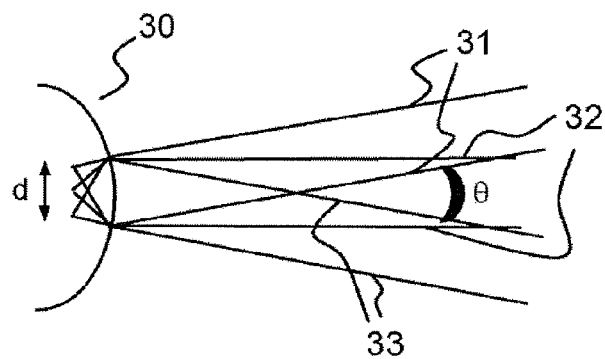
FIG. 3, a schematic illustrating the calculation of the size of the image of the imaging source formed by the corneal surface.

FIG. 3 schematically illustrates how the size of the image of the source formed by the corneal surface is calculated for the case of a collimated source of angular diameter $\theta$. The beams 31, 32, 33 are field edge beams (31, 33) and field center beams (32), respectively. The diameter d of the image is given by $d=\tan \theta \times R/2$ where R is the radius of curvature of the cornea (R=7.8 mm on average). Thus, in the case of a retinal camera imaging a field of 5×5° on the retina, the size of the image of the illuminating source on the retina, given by the preceding formula, is d=0.340 mm. In this case, the size of the dot is therefore set so that its image in the entrance space of the imaging optical system (or the exit space of the eye) is at least equal to 0.340 mm. In this case the percentage of the pupil that is blocked can be calculated to be about $(0.340/5)^2=0.5\%$, assuming an entrance pupil of 5 mm, which, as will be seen, has little effect on the quality of the image. Advantageously, a dot that is slightly larger will be chosen in order to compensate for errors created during production and/or alignment of the optical system. For example, the image of the dot in the entrance space of the imaging system will possibly have a diameter at least equal to 0.5 mm. In this case, the percentage blocked increases to 1%.

In the example in FIG. 2, a dot is provided by way of a blocking system. This dot may for example be integrated into a transparent strip having flat parallel sides. Other systems are obviously possible, for example a drilled mirror which could be placed in a plane conjugated with the correcting plane. The blocking area is round in principle, but it could be oval in the case where it is placed on a mirror operating at a nonzero incidence. The characteristics of the oval would then be calculated in order to obtain a blocking area that is round when it is projected onto a plane perpendicular to the optical axis.

In the example in FIG. 2, the blocking dot is centered on the optical axis of the imaging system. This position is preferable because the apex of the cornea is in general centered on the pupil of the eye, the eye advantageously being centered on the entrance pupil of the optical system.

Figure 4:
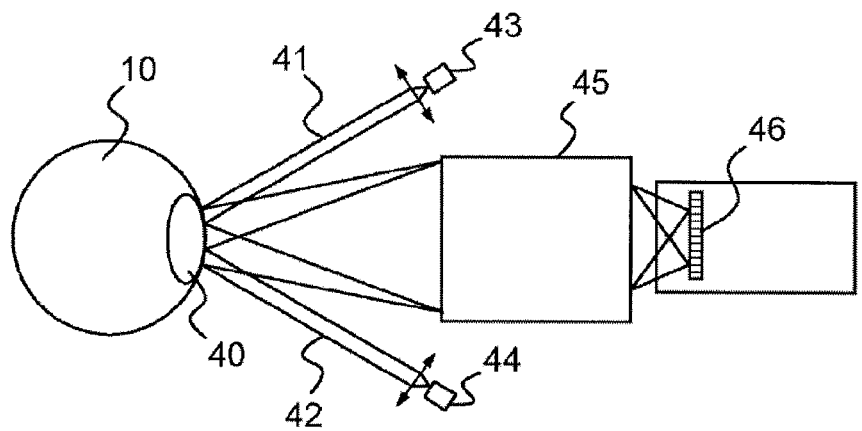
FIG. 4, a schematic illustrating an alignment system for use in one embodiment of the invention.

Advantageously, the retinal imaging device according to the invention comprises a system, such as shown in FIG. 2 (43, 44, 45, 46) or in FIG. 4, for spatially positioning the imaging system relative to the eye. In order for the blocking system to have its full effect, it is important for the imaging device to be placed in front of the eye to be measured in such a way that the image of the blocking system, projected onto the entrance space of the imaging optical system, which is the exit space of the eye, covers the image of the illuminating source formed by the corneal surface. It is therefore advantageous for the retinal imaging camera to possess a positioning system that enables this adjustment to be made. The positioning system (FIG. 4) for example comprises alignment sources 43, 44 coupled to a camera for visualizing the eye, comprising an objective lens 45 and a detector 46, for example a matrix detector. The alignment sources may, for example, be 2, 3 or 4 in number. They are imaged by the corneal surface 40 of the eye 10. Observation of the position of these images, by means of the camera 45, 46 for visualizing the eye, makes it possible to position the device.

Advantageously, the positioning system will possibly allow an operator or an image-processing software package coupled to a motorized system to position the imaging device in such a way that corneal reflections are blocked by the blocking system. If this operation is performed by the operator via a joystick, the image of the pupil of the eye may be overlaid with a small cross, for example, symbolizing the center of the blocking area. The operator will in this case be responsible for making the images of the corneal reflections related to the alignment sources clear and sharp by adjusting the distance between the instrument and the eye of the subject, and for placing these images either side of the cross by laterally adjusting the relative position of the instrument and the eye of the subject.

Figure 5A:
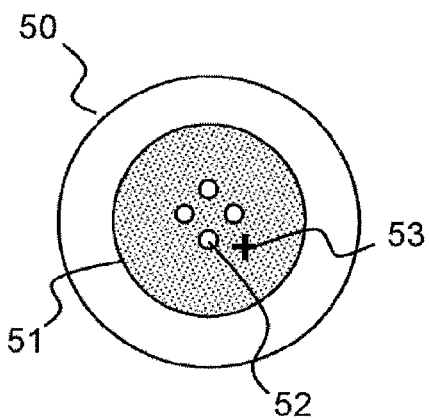
FIGS. 5A and 5B, two schematics showing an example alignment procedure implemented by the system in FIG. 4.
Figure 5B:
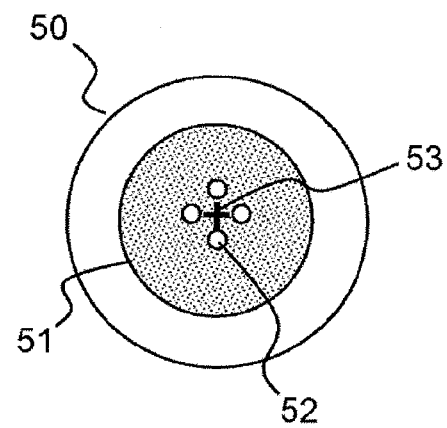

FIGS. 5A and 5B thus illustrate a first example (FIG. 5A) where the cross (referenced 53) is not centered relative to the images of the alignment sources 52 (4 in number in this example) and a second example where the alignment is corrected (FIG. 5B). In these examples, the reference 50 indicates the edge of the iris, and the reference 51 the edge of the pupil of the eye.

Figure 6:
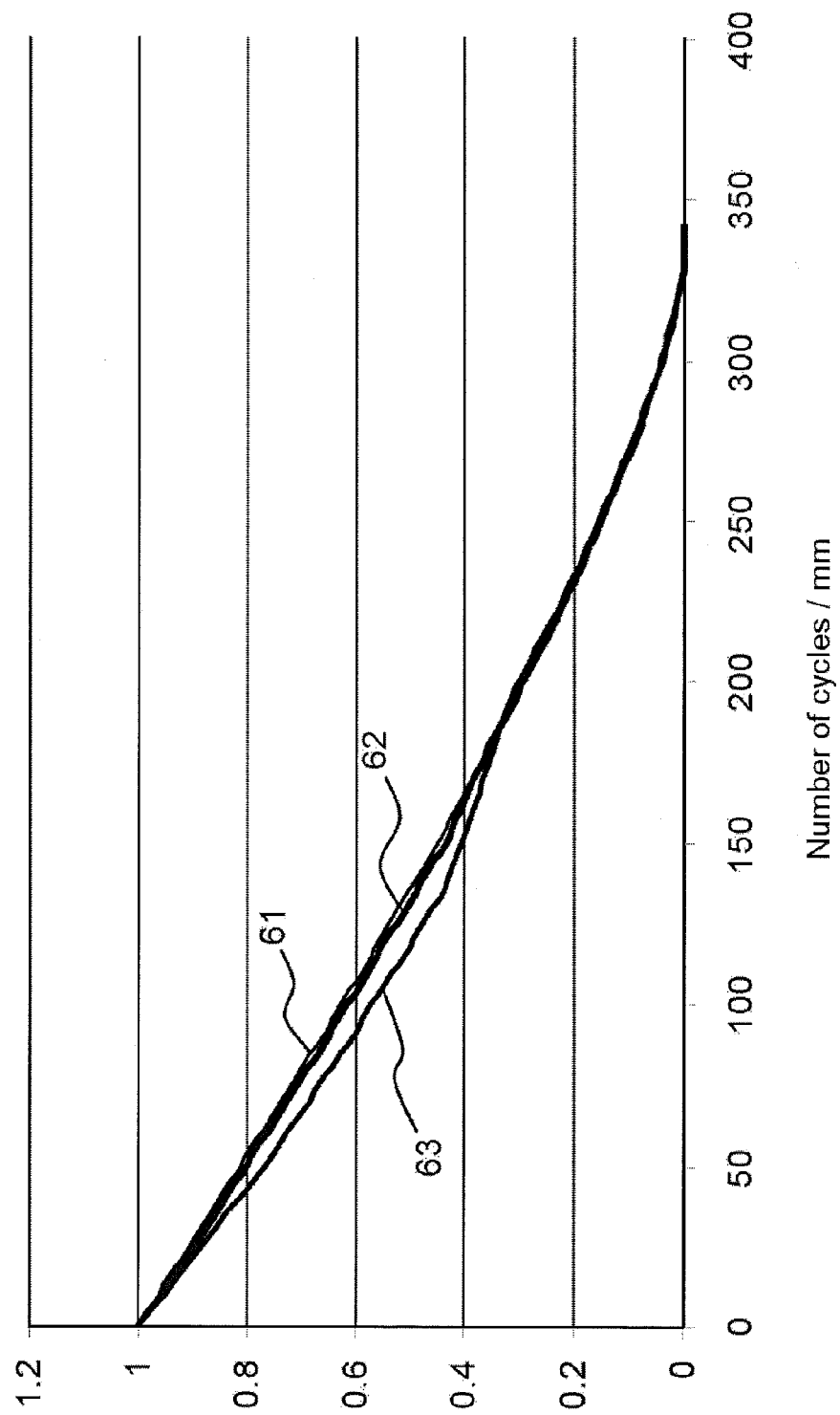
FIG. 6, a curve showing a comparison of the MTF calculated as a function of the frequency for a prior-art system and two example systems according to the invention.

The Applicant has moreover demonstrated that the effect of the blocking area on the MTF is negligible. A MTF simulation was carried out, with and without a blocking system, by means of the Zemax© software package, and the results are shown in FIG. 6. In this figure, the curve 61 shows the MTF calculated without blocking. The curve 62 shows the MTF calculated with a central blocking dot positioned in the correcting plane, the diameter of the image of which, projected onto the plane of the image of the imaging source formed by the corneal surface, was 0.5 mm. The curve 63 shows the MTF calculated with a blocking dot positioned on the correcting plane, the diameter of the image of which, projected onto the plane of the image of the imaging source formed by the corneal surface, was 1 mm. These calculations demonstrated that, relative to the perfect MTF curve without central blocking, the fact of having a central blocking area causes a slight drop in the MTF, in particular at low spatial frequencies, down to about half the cut-off frequency, and leads to a slight increase at high spatial frequencies, up to the cut-off frequency. However, for a blocking area of 0.5 mm diameter in the pupillary plane, the variation upward or downward remains completely negligible (less than 1% variation). Moreover, even with larger blocking areas (up to 1.3 mm), for high spatial frequencies (above half the cut-off frequency) the MTF remains just slightly above the perfect blocking-free MTF. The MTF drop only impacts spatial frequencies where the MTF is already above 40%, which does not adversely affect the imaging because the contrast is already very good for the spatial frequencies impacted by this drop in MTF.

The Applicant has moreover demonstrated that the loss of flux from the image formed by the camera, which is equal, in percentage, to the square of the ratio of the blocking diameter of the blocking system projected into the entrance space of the imaging system to the diameter of the entrance pupil, does not exceed 1% in the case of a diameter of 0.5 mm and an entrance pupil with a diameter of 5 mm. In contrast, the signal-to-noise ratio is greatly improved because removing corneal reflection substantially decreases noise.

It is possible to evaluate the increase in the quality of the image by way of the increase obtained in the signal-to-noise ratio. Experimentally, the total signal received by the detector in the presence of corneal reflections, in the case of a full-field imaging system comprising a 5 mm entrance pupil placed in the pupillary plane of the eye, and implementing a 4×4° (imaging) field illuminated with an illuminating beam centered on the apex of the cornea, may be decomposed into the following components:

- 42.3% of the signal detected by the detector is due to corneal reflection. This signal contains no useful information but adds detection noise;
- 50.7% of the signal detected by the detector is due to the retinal layers located above and below the photoreceptor layer. This signal contains no useful information but adds detection noise; and
- 7% of the signal detected by the detector is due to the photoreceptor layer that it is sought to image. This signal is the useful signal.

If $T_1$ is the total signal detected by the detector, the signal-to-noise ratio $SNR_1$ is expressed by the following relationship (neglecting detector read noise, which is negligible relative to the detection noise of the total signal, which is at least 5 to 10 times higher):

$$SNR_1 = \frac{\text{Signal}}{\text{Bruit}} = \frac{0{,}07 * T_1}{\sqrt{T_1}} = 0{,}07 * \frac{T_1}{\sqrt{T_1}}$$

The same calculation may be carried considering the addition of a blocking area, the diameter of the image of which, projected onto the pupillary plane, is 0.5 mm. The blocking area represents 1% of the entrance pupil and automatically causes a drop of 1% in the useful signal coming from the photoreceptor layer, and in the signal originating from the retinal layers located on either side of the photoreceptor layer. Because of the suppression of the corneal reflection and the central blocking, which obstructs 1% of the pupil, the total signal received $T_2$ in this new configuration is decreased and $T_2 = 0.57 \times T_1$. In this new configuration, the total signal $T_2$ received by the detector is now divided as follows:

- 87.8% of the signal detected by the detector is due to the retinal layers located above and below the photoreceptor layer. This signal contains no useful information but adds detection noise; and
- 12.2% of the signal detected by the detector is due to the photoreceptor layer that it is sought to image. This signal is the useful signal.

The new signal-to-noise ratio SNR2 is then expressed by the following relationship:

$$SNR_2 = \frac{\text{Signal}}{\text{Bruit}} = \frac{0{,}12 * T_2}{\sqrt{T_2}} = \frac{0{,}069 * T_1}{\sqrt{0{,}57 * T_1}} = 0{,}092 * \frac{T_1}{\sqrt{T_1}} = 1{,}31 * SNR_1$$

The increase related to the addition of the central blocking area is therefore more than 30%.

Figure 7A:
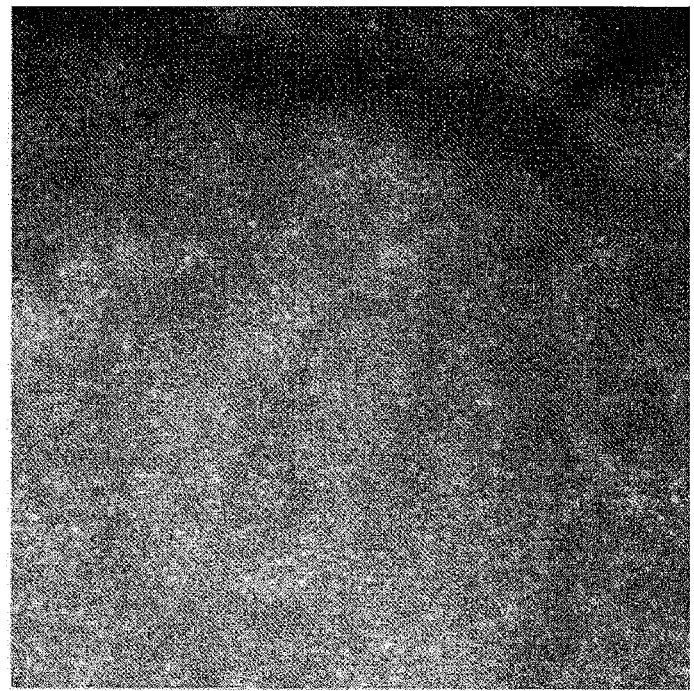
FIGS. 7A and 7B, retinal images measured using full-field retinal imaging systems at 850 nm, with a prior-art system and with a system according to the invention, respectively.
Figure 7B:
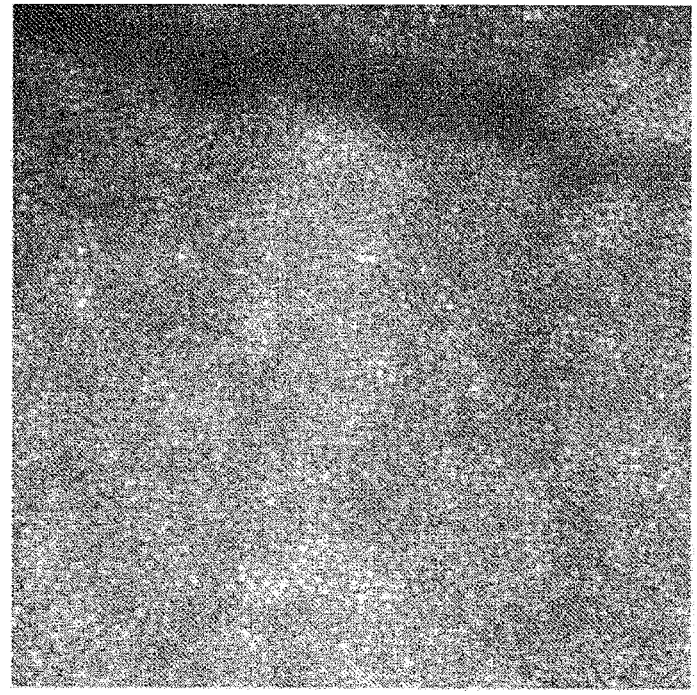

The two raw (neither processed nor averaged) images shown in FIGS. 7A and 7B allow the improvement in the quality of the images obtained, due to the blocking system, to be evaluated.

The first image (7A) was produced with a high-resolution full-field imaging camera not equipped with a blocking system. The flux for illuminating the retina was input via the apex of the cornea, and the illumination enabling measurement of optical defects was injected off-axis so that corneal reflections for this illuminating source did not interfere with the measurement. The analysis and illuminating sources were triggered in succession and the system for measuring optical defects was synchronized with the analysis illuminating source whereas the detector forming the image of the retina was triggered with the source illuminating the retina.

The second image (7B) was produced with exactly the same system used to take the first image, but a blocking dot was added to a plane in the immediate vicinity of the plane of the correcting system (i.e. a pupillary plane). The diameter of this blocking area projected into the space of the eye was 1 mm. Moreover, the analysis source was re-centered and input via the apex of the cornea, enabling the Stiles-Crawford effect obtained for this signal to be optimized. Corneal reflections related to this signal were blocked by the blocking system and did not interfere with the optical defect measurement.

A notable improvement may be seen in FIG. 7B.

It will be noted that this study focused on corneal reflection, the cornea being a diopter that it is absolutely impossible to avoid when the illuminating the retina; however, the same reasoning applies to any diopter common to imaging and illuminating optical paths.

Advantageously, the retinal imaging method according to the invention comprises a calibration phase, during which a control-loop software program, allowing the correcting device to be controlled, "learns" how the system for measuring optical defects measures the variation in the response of the correcting system when each of the actuators is actuated one by one. For reasons of rapidity of convergence and of final correction quality, it is advantageous to carry out this calibration of the control loop without the central blocking area fitted. As a variant, the calibration may be carried out using an artificial eye instead and in place of the eye of the subject, in which case the central blocking area will necessarily be fitted. As another variant, a specific calibration channel may be used to calibrate the adaptive optical system, as is the case, for example, in the example in FIG. 2. The calibration channel comprises an internal source $LS_c$ placed at the focal point of optics $L_8$, and a beam splitter $BS_4$ allowing the calibration beam originating from the calibration source to be transmitted to the deformable mirror 14, then to the device 15 for measuring optical defects. In this case, it is necessary for the optical path between the internal source $LS_c$ and the system for measuring optical defects to pass both via the correcting system and via the blocking system. Of course, when the blocking system is placed on or in the immediate vicinity of the correcting plane of the correcting system, this constraint is met. This is another reason for placing the blocking system in this particular position.

Although described by way of a number of detailed embodiments, the retinal imaging device and method according to the invention comprise various variants, modifications and improvements that will be obvious to those skilled in the art, it being understood that these various variants, modifications and improvements form part of the scope of the invention such as defined by the following claims.

In particular, the invention was described by taking the example of a retinal imaging device to which it was particularly applicable because of the importance of reducing corneal reflections in the imaging channel, but it may also be applied to AOSLO or OCT systems using adaptive optics, or more generally to any retinal image device using adaptive optics, in which reduction of corneal reflections in the analysis channel and, to a lesser extent, in the imaging channel, is also necessary to increase image quality.

The invention claimed is:

1. A retinal imaging device comprising:
   at least one source for emitting a light beam for illuminating the retina of an eye of a subject;
   an imaging channel for imaging the retina, comprising a detecting device with a detecting plane, and an imaging optical system;
   an analysis channel, comprising a device for measuring optical defects, with an analysis plane intended to receive a set of light rays backscattered by the retina, and means for optically conjugating said analysis plane with a preset plane in the entrance space of said imaging system of the imaging channel;
   a correcting device common to said analysis and imaging channels, comprising a correcting plane, and intended to correct, in said correcting plane, the light rays originating from said emitting source and backscattered by the retina, depending on optical defects measured by the device for measuring optical defects; and
   a system for blocking light, positioned in a plane neighboring or coincident with said correcting plane, or in an image plane of said correcting plane located on an optical path common to the analysis and imaging channels, and dimensioned to at least partially block reflection by the corneal surface of light rays originating from said emitting source.

2. The device as claimed in claim 1, in which said correcting plane is conjugated with said preset plane in the entrance space of the imaging system of the imaging channel.

3. The device as claimed in claim 2, in which said preset plane is the plane of the entrance pupil of said imaging system.

4. The device as claimed in claim 1, wherein the blocking system takes the form of an opaque disk the diameter of which, projected into the entrance space of the imaging system, is greater than or equal to a value d given by $d = \tan\theta \times R/2$, where R is the radius of curvature of the cornea and $\theta$ is the angular diameter of the emitting source.

5. The device as claimed in claim 1, wherein the blocking system is centered on the optical axis of said imaging optical system.

6. The device as claimed in claim 1, wherein the correcting device comprises a deformable mirror.

7. The device as claimed in claim 1, wherein the device for measuring optical defects is a Shack-Hartmann analyzer.

8. The device as claimed in claim 1, further comprising a system for positioning the imaging device in space relative to the eye.

9. The device as claimed in claim 1, wherein the retinal imaging device is of the full-field type, comprising an imaging first light source for illuminating a given field of the retina, and an analysis second light source for illuminating the retina for the purpose of analyzing optical defects with said device for measuring optical defects, the detecting device comprising a matrix detector and the blocking system being dimensioned to at least partially block reflection by the corneal surface of the light rays originating from said sources.

10. A retinal imaging method, comprising:
    emitting at least one light beam in order to illuminate the retina of an eye of a subject, by means of light-emitting source;
    forming an image of at least one part of the retina on a detecting plane of a detecting device, by means of an imaging optical system defining an imaging channel;
    measuring optical defects by analyzing, in a given analysis plane, optical defects in light rays backscattered by the retina, said analysis plane being conjugated with a preset plane of the eye by means of an optically conjugating system defining an analysis channel;
    correcting, in a given correcting plane, light rays originating from said emitting source and backscattered by the retina, depending on the measured optical defects; and
    at least partially blocking reflection by the corneal surface of light rays originating from said emitting source using a system for blocking light flux, said system being arranged in a plane neighboring the correcting plane, or in a plane conjugated with the correcting plane located on a path common to the analysis and imaging channels.

11. The retinal imaging method as claimed in claim 10, in which the correcting plane is conjugated with said preset plane of the eye.

12. The retinal imaging method as claimed in claim 11, in which said preset plane of the eye is substantially coincident with the image plane of said light-emitting source formed by the corneal surface.

13. The retinal imaging method as claimed in claim 10, wherein said preset plane of the eye is substantially coincident with the plane of the entrance pupil of the imaging system.

14. The retinal imaging method as claimed in claim 10, wherein the beams originating from said light-emitting source are incident into the eye via the apex of the cornea of the eye.

15. The retinal imaging method as claimed in claim 10, further comprising positioning said imaging system in space relative to the eye.

16. The retinal imaging method as claimed in claim 10, further comprising emitting an imaging first light beam in order to illuminate a given field of the retina, and emitting a second light beam for illuminating the retina for the purpose of analyzing optical defects, and at least partially blocking reflection by the corneal surface of said imaging and analysis light beams using said blocking system.

* * * * *